(12) United States Patent
Li et al.

(10) Patent No.: US 11,266,396 B2
(45) Date of Patent: Mar. 8, 2022

(54) INTRAORAL RETRACTOR FOR TEMPOROMANDIBULAR JOINT

(71) Applicant: CHAMFOND BIOTECH CO., LTD, Jiangsu (CN)

(72) Inventors: Longjiang Li, Jiangsu (CN); Jianhua Zhang, Jiangsu (CN); Fengchang Liu, Jiangsu (CN); Wenke Zhang, Jiangsu (CN)

(73) Assignee: CHAMFOND BIOTECH CO., LTD, Jiangsu (CN)

( * ) Notice: Subject to any disclaimer, the term of this patent is extended or adjusted under 35 U.S.C. 154(b) by 111 days.

(21) Appl. No.: 16/762,824

(22) PCT Filed: Oct. 25, 2018

(86) PCT No.: PCT/CN2018/111770
§ 371 (c)(1),
(2) Date: May 8, 2020

(87) PCT Pub. No.: WO2019/091286
PCT Pub. Date: May 16, 2019

(65) Prior Publication Data
US 2020/0383673 A1    Dec. 10, 2020

(30) Foreign Application Priority Data

Nov. 8, 2017 (CN) .......................... 201711089414.6
Dec. 12, 2017 (CN) .......................... 201711321676.0

(51) Int. Cl.
*A61B 17/02* (2006.01)
*A61B 17/24* (2006.01)

(52) U.S. Cl.
CPC ............ *A61B 17/025* (2013.01); *A61B 17/24* (2013.01)

(58) Field of Classification Search
CPC ... A61B 17/02; A61B 17/0218; A61B 17/025; A61B 17/24; A61B 17/56
See application file for complete search history.

(56) References Cited

U.S. PATENT DOCUMENTS 6,558,392 B1    5/2003 Martini
2007/0010715 A1*  1/2007 Sixto, Jr. .............. A61B 17/068
                                                600/217

FOREIGN PATENT DOCUMENTS

CN    201691968 U    1/2011
CN    201899527 U    7/2011
(Continued)

*Primary Examiner* — Larry E Waggle, Jr.
(74) *Attorney, Agent, or Firm* — Muncy, Geissler, Olds & Lowe, P.C.

(57) ABSTRACT

The invention discloses an intraoral retractor for a temporomandibular joint and relates to the technical field of medical instruments. The invention comprises a retraction mechanism, a main connecting rod and an operating mechanism; wherein the retraction mechanism and the main connecting rod are bent overall, one end of the retraction mechanism is a supporting end, and the other end is connected with the main connecting rod; a draw hook in a withdrawn state is provided in the supporting end, the operating mechanism is disposed at a tail end of the main connecting rod, and the operating mechanism can enable the draw hook to thrust out of the retraction mechanism and move up and down in the supporting end. The invention has a small size with the overall structure designed as a small bent pipe, the bending angle fits features of a human body, only a small incision is required for the retractor to enter the oral cavity of a patient, so the patient may suffer less pain, and no scar is left on the patient's face.

21 Claims, 5 Drawing Sheets

(56) References Cited

FOREIGN PATENT DOCUMENTS

| CN | 102499730 A | 6/2012 |
|---|---|---|
| CN | 204797916 U | 11/2015 |
| CN | 105380589 A | 3/2016 |
| CN | 108175457 A | 6/2018 |
| DE | 42 10 723 A1 | 10/1993 |
| WO | WO 93/20755 A1 | 10/1993 |

* cited by examiner

INTRAORAL RETRACTOR FOR TEMPOROMANDIBULAR JOINT

TECHNICAL FIELD

The invention relates to the technical field of medical instruments, and particularly to a surgical instrument for maxillofacial surgery.

BACKGROUND ART

Mandibular condylar fracture is a maxillofacial fracture of high incidence. The condylar fracture causes reduced occlusal function and limited opening of the mouth. If not taken operation immediately, the fracture may be displaced by the muscle under a traction force, serious consequences such as facial deformity may occur, leading to great harm to a patient.

Generally, there are two common operations for treating mandibular condylar fractures. According to one operation, an incision is made on the face of a person to fully expose a broken end of the fracture, and then the condyle is repositioned and fixed. The disadvantages of this operation are that facial nerves may be damaged, and an obvious scar may be left on the face of the person after the operation, causing great negative side effects to the patient. According to the other operation, the mandible is retracted by hand to expose a gap of the mandibular joint and find out the broken end of the condyle for reposition. However, retraction by hand is unstable and the force application point is not easy to control, causing difficulties in exposing the gap of the joint, longer duration of the operation, and greater risks.

The Chinese patent No. 201410353406 discloses a mandibular condyle reposition expander, including a lower supporting and combining portion and an upper supporting and combining portion corresponding to the incisura of the underjaw and the zygomatic arch of the human body, wherein a front end and a rear end of the upper and the lower supporting and combining portions are hinged with support rods, the support rod is in threaded connection with a central shaft, and moves on the central shaft through a worm gear and worm mechanism to achieve the supporting and combining function. However, the expander occupies a large space, which means a large incision has to be made to allow the operation, an operator may have difficulties in holding it, and the degree of expansion cannot be visually seen from the outside, as a result, the efficiency of the operation is reduced.

SUMMARY OF THE INVENTION

It's an object of the invention to provide an intraoral retractor for a temporomandibular joint, featuring small size, facilitated accurate operation, and precision and stability in work.

Specifically, the invention is realized by implementing the following technical solution: the intraoral retractor comprises a retraction mechanism, a main connecting rod, and an operating mechanism; wherein the retraction mechanism and the main connecting rod are bent overall, one end of the retraction mechanism is a supporting end, and the other end is connected with the main connecting rod; a draw hook in a withdrawn state is provided in the supporting end, the operating mechanism is disposed at a tail end of the main connecting rod, and the operating mechanism can enable the draw hook to thrust out of the retraction mechanism and move up and down in the supporting end. The retraction mechanism has a slender profile, and an outer diameter of the retraction mechanism is smaller than a gap between a mandibular ramus and a tail end of a mandible to facilitate access to a target position.

Furthermore, the operating mechanism is connected with the draw hook through a wire and controls movement of the draw hook by drawing the wire.

Furthermore, a pin shaft capable of moving up and down in the supporting end is further provided in the supporting end of the retraction mechanism, and the draw hook is hinged with the pin shaft.

Furthermore, the wire is inserted into the draw hook through a round head.

Furthermore, an elastic member capable of resetting the draw hook is further provided in the supporting end of the retraction mechanism.

Furthermore, the elastic member is a spring provided below the draw hook.

Furthermore, a surface of the supporting end of the retraction mechanism is provided with a slot, and the draw hook thrusts out of the retraction mechanism from the slot.

Furthermore, a top of the supporting end is a supporting bevel.

Furthermore, the supporting bevel is provided with an irregular convex structure resembling a diamond surface.

Furthermore, an overall bending angle of the retraction mechanism and the main connecting rod allows the mandible to be retracted approximately vertically downwards. And the retraction mechanism acts at a sigmoid notch of the mandible of a human skull.

Furthermore, the wire is a steel wire.

Furthermore, the operating mechanism comprises a first slider sleeved on the tail end of the main connecting rod and a first rotational handle sleeved outside the first slider, the first slider can slide on the tail end of the main connecting rod and is in threaded transmission with the first rotational handle, and the wire connects the first slider.

Furthermore, the tail end of the main connecting rod is an oval shaft, and the first slider is matched with the oval shaft, so that the first slider can move linearly without rotating.

Furthermore, a scale ruler is provided behind the first slider.

Furthermore, an adjusting screw for adjusting the tension of the wire is provided between the first slider and the wire.

Furthermore, the adjusting screw has a hexagonal outer profile.

Furthermore, the main connecting rod is further provided with a first fixed handle.

Furthermore, the operating mechanism comprises a second rotational handle sleeved on the tail end of the main connecting rod and a third slider inserted into the tail end of the main connecting rod, the second rotational handle is in threaded transmission with the tail end of the main connecting rod, the third slider is connected with a lower portion of the second rotational handle, and the wire connects the third slider.

Furthermore, the wire forms a closed loop inside the retractor, and the operating mechanism comprises a second slider connected with the wire.

Furthermore, the wire is tensioned by pins, and the pins are provided at two ends in the retractor, respectively.

Furthermore, the operating mechanism comprises a second fixed handle provided at the tail end of the main connecting rod and a movable handle hinged with the second fixed handle, and the wire connects an end of the movable handle.

The invention has the following advantages: the intraoral retractor for the temporomandibular joint disclosed by the invention has a small size with the overall structure designed as a small bent pipe, the bending angle fits features of a human body, only a small incision is required for the retractor to enter the oral cavity of a patient, so the patient may suffer less pain, and no scar is left on the patient's face; supported by the skull base, the retractor vertically retracts the mandible, catering to the stress condition of facial muscles better and featuring improved reliability during working; the operating mechanism is operated outside the oral cavity of a person conveniently, and the design of the scale ruler at the tail end of the retractor can render the degree of retraction visually observed.

DETAILED DESCRIPTION OF THE INVENTION

Figure 1:
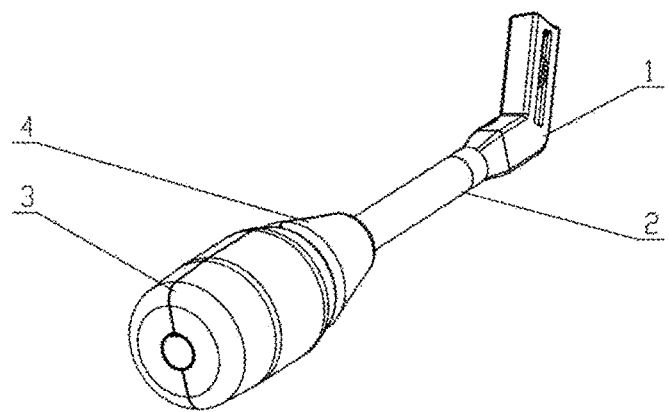
FIG. 1 is a schematic view showing an overall structure of Embodiment 1 of the present invention.

The invention will now be described in further detail with reference to Embodiments and the accompanying drawings.

Embodiment 1

An embodiment of the invention is an intraoral retractor for a temporomandibular joint for maxillofacial surgery. Referring to FIGS. 1, 2, 3 and 4, the intraoral retractor for the temporomandibular joint has an overall profile of a slender bent pipe, including a retraction mechanism 1, a main connecting rod 2, a first rotational handle 3 and a first fixed handle 4.
The retraction mechanism 1 is bent and slender, an outer diameter of the retraction mechanism 1 is smaller than a gap between a mandibular ramus and a tail end of a mandible, the bending angle fits features of a human body, thereby facilitating access to a target position and allowing the mandible to be retracted approximately vertically downwards. One end of the retraction mechanism 1 is a supporting end and is used for fitting the human skull base, and the other end is connected with the main connecting rod 2. The top of the supporting end is a supporting bevel 7 that fits the human skull base. In order to increase the stability of the support, an irregular convex structure resembling a diamond surface is provided on the supporting bevel 7 in this Embodiment to increase the friction force on contacted surfaces, and the retractor of the invention can thus operate more stably. The retraction mechanism 1 is supposed to be small enough to reduce the size of the surgical incision and facilitate adjustment of the working position A slot is formed in the surface of the supporting end of the retraction mechanism 1, a pin shaft 8, a draw hook 5, a wire 9 and a spring 14 are provided in the slot, the pin shaft 8 can move up and down in the supporting end, and the draw hook 5 is hinged with the pin shaft 8. The wire 9 is used to pull the draw hook 5 to move, which requires sufficient strength, for example, a steel wire is adopted, and the wire is inserted into the draw hook 5 through a round head 10 to avoid interference with the wire 9 as the draw hook 5 rotates.

In an initial state, the draw hook 5 is hidden in the supporting end, if the draw wire 9 is pulled then, the draw hook 5 rotates around the pin 8 and gradually the head of the draw hook 5 thrusts out of the retraction mechanism 1 from the slot in the surface of the supporting end. When the draw hook 5 rotates by 90 degrees around the pin 8, the wire 9 is further pulled, at this moment, the draw hook 5 drives the pin 8 to move downwards in the supporting end, with the movement track thereof controlled by the profile of the slot formed in the surface of the supporting end. It can be seen that both rotation and linear movement of the draw hook 5 can be realized by pulling the draw wire 9.

The spring 14 is provided below the draw hook 5 and passes the wire 9 therethrough, acting to impart an upward force to the draw hook 5 to reset the draw hook 5 when the wire 9 is not tensioned. The spring 14 may also be replaced by an elastic member such as a rubber band, and the position of the spring 14 may be specifically determined according to the implementation of the elastic force.

Figure 2:
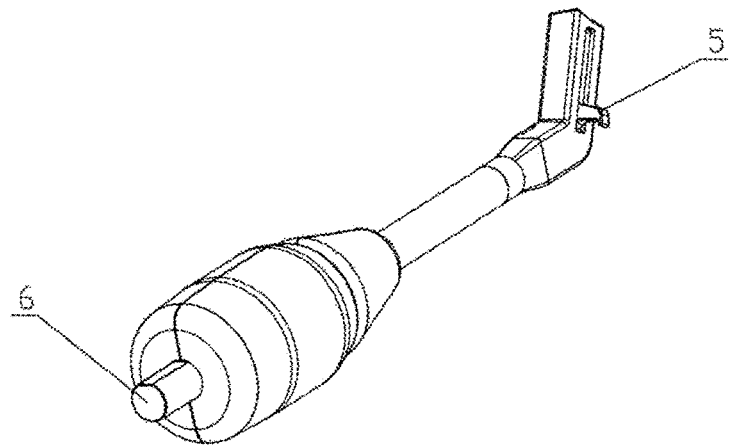
FIG. 2 is a schematic view showing a working state of Embodiment 1 of the present invention.
Figure 3:
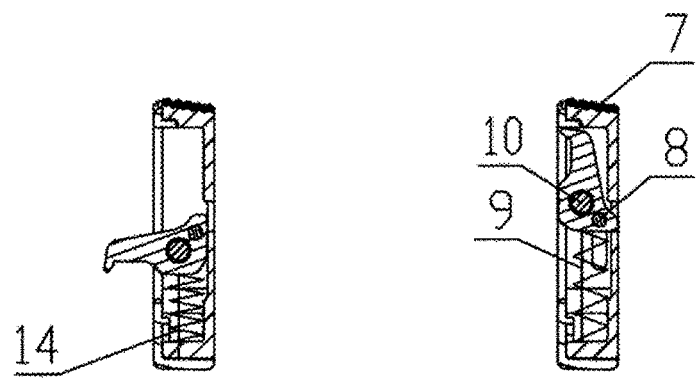
FIG. 3 is a schematic view showing the working state of a retractor of the present invention.

Referring to FIGS. 1 and 2, one end of the main connecting rod 2 is connected with the retraction mechanism 1, and the other end is provided with a first fixed handle 4 and a first rotational handle 3 sequentially. The first fixed handle 4 serves to facilitate holding the retractor during operation.

Figure 4:
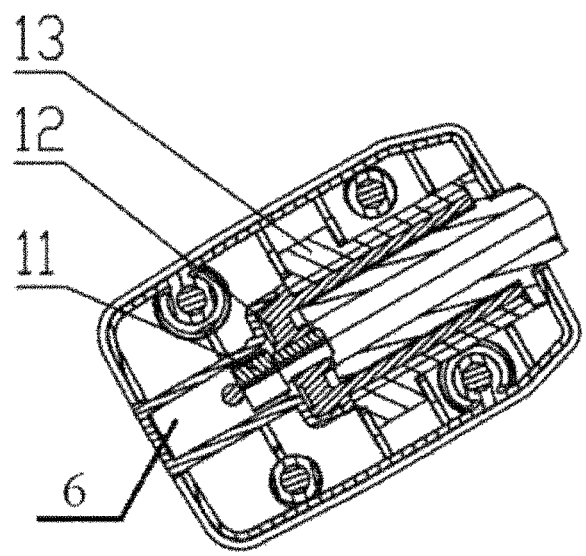
FIG. 4 is a schematic view showing a rotational handle of Embodiment 1 of the present invention.

Referring to FIG. 4, the tail end of the main connecting rod 2 is designed as an oval shaft on which the first slider 12 is sleeved in sliding fit with the tail end of the main connecting rod 2, so that the first slider 12 can slide freely without rotating on the oval shaft. The wire 9 is threaded from the supporting end of the retraction mechanism 1 all the way into the main connecting rod 2 and reaches out of the tail end of the main connecting rod 2 to connect the first slider 12.

The first rotational handle 3 is sleeved outside the first slider 12, and a drum 13 is fixed inside the first rotational handle 3. The surface of the first slider 12 is provided with threads to form threaded transmission with the drum 13, and the transmission renders reasonable stress and self-locking. When the first rotational handle 3 is rotated, the drum 13 rotates together, thereby driving the first slider 12 to slide axially along the main connecting rod 2, and the wire 9 is pulled.

An adjusting screw 11 is connected between the first slider 12 and the wire 9 through threads for adjusting the tension of the wire 9. In this embodiment, the adjusting screw 11 has a hexagonal outer profile and can adjust by using a mating sleeve.

A scale ruler 6 is provided behind the first slider 12, hidden inside the first rotational handle 3 in the initial position, and slides with the first slider 12 in operation. When the scale ruler 6 slides out of the first rotational handle 3, the corresponding sliding distance can be observed, as shown in FIG. 2.

Figure 8:
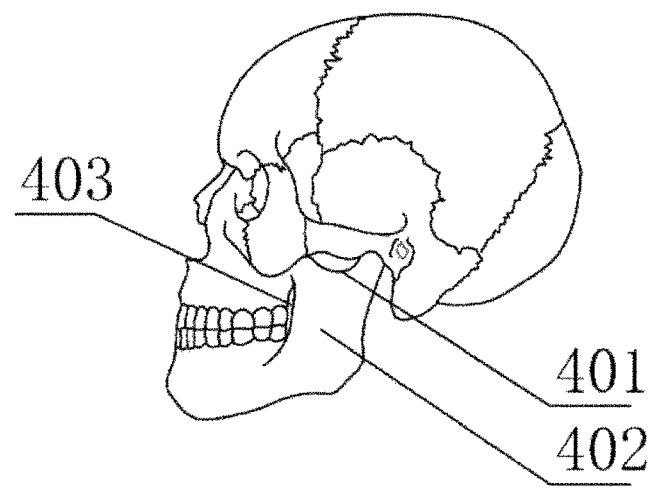
FIG. 8 is a side view showing a human skull (including mandible) of an embodiment of the present invention.
Figure 9:
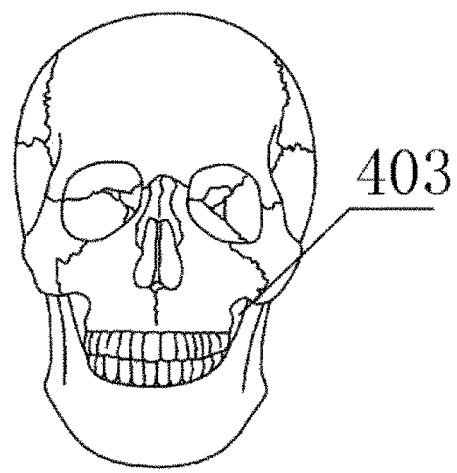
FIG. 9 is a front view showing a human skull of an embodiment of the present invention.
Figure 10:
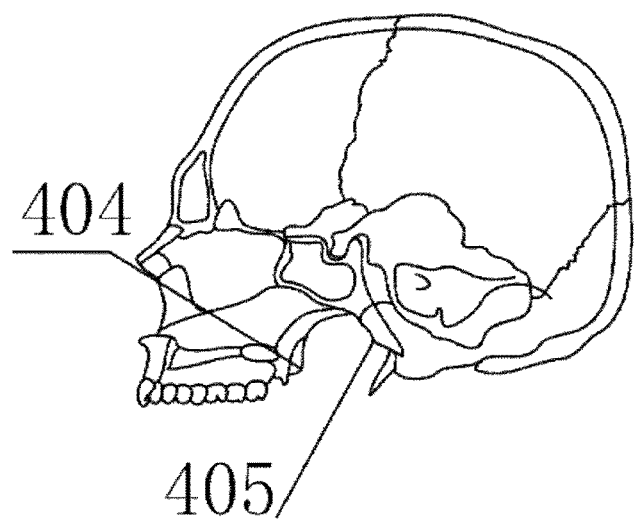
FIG. 10 is a side view showing a human skull (without mandible) of an embodiment of the present invention.
Reference numerals in the drawings: 1—retraction mechanism, 2—main connecting rod, 3—first rotational handle, 4—first fixed handle, 5—draw hook, 6—scale ruler, 7—supporting bevel, 8—pin shaft, 9—wire, 10—round head, 11—adjusting screw, 12—first slider, 13—drum, 14—spring, 100—second slider, 101—pin, 200—movable handle, 201—second fixed handle, 202—hinge, 300—sleeve, 301—third slider, 302—second rotational handle, 303—connecting shaft, 401—mandibular sigmoid notch, 402—mandibular ramus, 403—surgical gap, 404—tail end of mandible, 405—skull base.

Referring to FIGS. 8, 9 and 10, the intraoral retractor for the temporomandibular joint of the present embodiment is used in the following manner: an operator grasps the retractor by the handle, reaches the retractor into the oral cavity of the patient, passes the retractor through the surgical gap 403 between the mandibular ramus 402 and the tail end of the mandible 404 to the vicinity of the target surgical area, and adjusts the position of the retractor so that the supporting bevel 7 at the top of the retraction mechanism 1 fits and remains stable against the skull base 405 of the patient, and the tail end of the main connecting rod 2 remains outside of the oral cavity of the patient. After this, the operator holds the first fixed handle 4, rotates the first rotational handle to pull the wire 9 such that the draw hook 5 thrusts out of the retraction mechanism 1 and hooks the sigmoid notch 401 of the mandible of the patient, the operator continues to rotate the first rotational handle 3 to open the mandible to a proper position, and the degree of opening of the mandible can be observed through the scale ruler 6 extending from the rear end of the retractor, and at this moment, the operation may start. When the operation is finished, the first rotational handle 3 is rotated reversely, so that the draw hook 5 is restored to be hidden in the supporting end of the retraction mechanism 1, the retractor is pulled out, and the operation is finished.

Embodiment 2

Another embodiment of the present invention, based on substantially the same principles as Embodiment 1, has substantially the same retraction mechanism 1 and main connecting rod 2 as Embodiment 1, except mainly for the operating mode for moving the draw hook 5.

Figure 5:
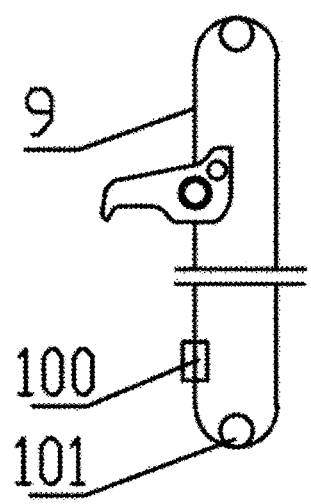
FIG. 5 is a schematic view showing an operation of Embodiment 2 of the present invention.

As shown in FIG. 5, in the present embodiment, a closed-loop wire 9 is used to realize the movement of the draw hook 5, that is, the wire 9 is a closed loop in the retractor, the draw hook 5 is provided on the wire 9, and pins 101 are used to tension the wire 9 at both ends (i.e., the top of the retraction mechanism 1 and the end of the main connecting rod 2) of the retractor, respectively. A second slider 100 is provided near the tail end of the main connecting rod 2 and is connected with the wire 9, the wire 9 can be enabled to move up and down as a closed loop by pushing or pulling the second slider 100, and the draw hook 5 can also be enabled to move accordingly.

Embodiment 3

Figure 6:
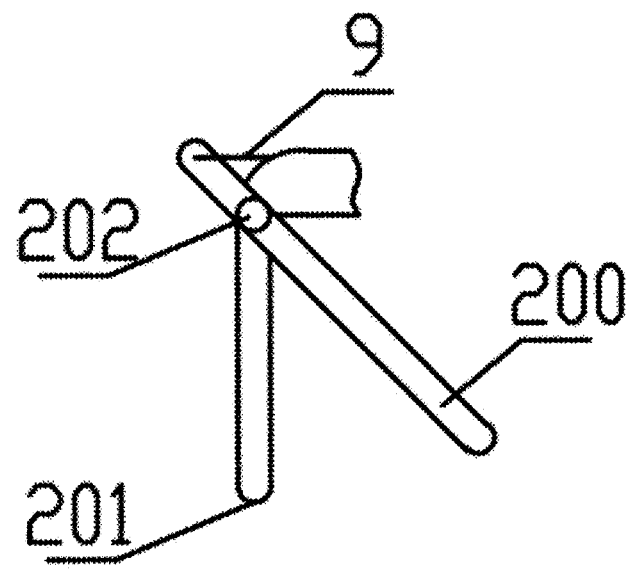
FIG. 6 is a schematic view showing an operation of Embodiment 3 of the present invention.

Another embodiment of the present invention, based on substantially the same principles as Embodiment 1, has substantially the same retraction mechanism 1 and main connecting rod 2 as Embodiment 1, except for the use of the first rotational handle 3 and the first fixed handle 4; instead, a second fixed handle 201 is provided at the end of the main connecting rod 2, and a movable handle 200 is hinged with the second fixed handle 201 through a hinge 202, the wire 9 is connected with one end of the movable handle 200, and the wire 9 is pulled by rotating the other end of the movable handle 200 using leverage, as shown in FIG. 6.

Embodiment 4

An embodiment of the present invention, based on substantially the same principles as Embodiment 1, has substantially the same retraction mechanism 1 and main connecting rod 2 as Embodiment 1, except mainly for the implementation of the rotational handle.

Figure 7:
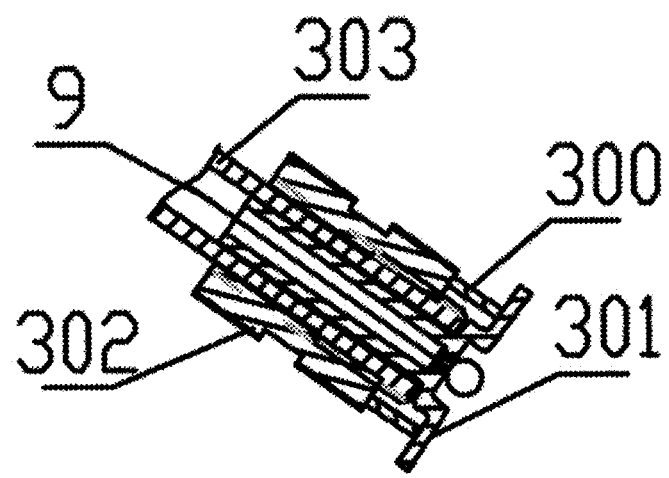
FIG. 7 is a schematic view showing an operation of Embodiment 4 of the present invention.

As shown in FIG. 7, the tail end of the main connecting rod 2 is a connecting shaft 303, and the outer surface of the connecting shaft 303 is provided with threads. A second rotational handle 302 is sleeved outside the connecting shaft 303, and the second rotational handle 302 is in threaded transmission with the connecting shaft 303. The bottom of the second rotational handle 302 is provided with a sleeve 300, the bottom of the sleeve 300 is connected with a third slider 301 inserted into the connecting shaft 303, and the wire 9 is connected with the third slider 301. When the second rotational handle 302 is rotated, the second rotational handle 302 pushes the sleeve 300, thereby causing the third slider 301 to move to pull the wire 9.

Although the present invention has been described above with reference to preferred embodiments, the embodiments are not intended to limit the invention. It is intended that those equivalent modifications and variations of this invention made without departing the spirit and scope of the invention shall fall within the scope of this invention. The scope of the invention shall, therefore, be determined according to the appended claims.

The invention claimed is:

1. An intraoral retractor for a temporomandibular joint, comprising a retraction mechanism, a main connecting rod, and an operating mechanism, wherein: the retraction mechanism and the main connecting rod are bent overall, one end of the retraction mechanism is a supporting end, and the other end is connected with the main connecting rod; a draw hook in a withdrawn state is provided in the supporting end, the operating mechanism is disposed at a tail end of the main connecting rod, and the operating mechanism can enable the draw hook to thrust out of the retraction mechanism and move up and down in the supporting end.

2. The intraoral retractor for the temporomandibular joint according to claim 1, wherein: the operating mechanism is connected with the draw hook through a wire and controls movement of the draw hook by drawing the wire.

3. The intraoral retractor for the temporomandibular joint according to claim 2, wherein: a pin shaft capable of moving up and down in the supporting end is further provided in the supporting end of the retraction mechanism, and the draw hook is hinged with the pin shaft.

4. The intraoral retractor for the temporomandibular joint according to claim 2, wherein: the wire is inserted into the draw hook through a round head.

5. The intraoral retractor for the temporomandibular joint according to claim 2, wherein: an elastic member capable of resetting the draw hook is further provided in the supporting end of the retraction mechanism.

6. The intraoral retractor for the temporomandibular joint according to claim 5, wherein: the elastic member is a spring provided below the draw hook.

7. The intraoral retractor for the temporomandibular joint according to claim 2, wherein: a surface of the supporting end of the retraction mechanism is provided with a slot, and the draw hook thrusts out of the retraction mechanism from the slot.

8. The intraoral retractor for the temporomandibular joint according to claim 2, wherein: a top of the supporting end is a supporting bevel.

9. The intraoral retractor for the temporomandibular joint according to claim 8, wherein: the supporting bevel is provided with an irregular convex structure resembling a diamond surface.

10. The intraoral retractor for the temporomandibular joint according to claim 2, wherein: an overall bending angle of the retraction mechanism and the main connecting rod allows a mandible to be retracted approximately vertically downwards.

11. The intraoral retractor for the temporomandibular joint according to claim 2, wherein: the wire is a steel wire.

12. The intraoral retractor for the temporomandibular joint according to claim 2, wherein: the operating mechanism comprises a first slider sleeved on the tail end of the main connecting rod and a first rotational handle sleeved outside the first slider, the first slider can slide on the tail end of the main connecting rod and is in threaded transmission with the first rotational handle, and the wire connects the first slider.

13. The intraoral retractor for the temporomandibular joint according to claim 12, wherein: the tail end of the main connecting rod is an oval shaft, and the first slider is matched with the oval shaft.

14. The intraoral retractor for the temporomandibular joint according to claim 12, wherein: a scale ruler is provided behind the first slider.

15. The intraoral retractor for the temporomandibular joint according to claim 12, wherein: an adjusting screw for adjusting tension of the wire is provided between the first slider and the wire.

16. The intraoral retractor for the temporomandibular joint according to claim 15, wherein: the adjusting screw has a hexagonal outer profile.

17. The intraoral retractor for the temporomandibular joint according to claim 12, wherein: the main connecting rod is also provided with a first fixed handle.

18. The intraoral retractor for the temporomandibular joint according to claim 2, wherein: the operating mechanism comprises a second rotational handle sleeved on the tail end of the main connecting rod and a third slider inserted into the tail end of the main connecting rod, the second rotational handle is in threaded transmission with the tail end of the main connecting rod, the third slider is connected with a lower portion of the second rotational handle, and the wire connects the third slider.

19. The intraoral retractor for the temporomandibular joint according to claim 2, wherein: the wire forms a closed loop inside the retractor, and the operating mechanism comprises a second slider connected with the wire.

20. The intraoral retractor for the temporomandibular joint according to claim 19, wherein: the wire is tensioned by pins, and the pins are provided at two ends in the retractor, respectively.

21. The intraoral retractor for the temporomandibular joint according to claim 2, wherein: the operating mechanism comprises a second fixed handle provided at the tail end of the main connecting rod and a movable handle hinged with the second fixed handle, and the wire connects an end of the movable handle.

\* \* \* \* \*